(12) United States Patent
Moszner et al.

(10) Patent No.: US 9,333,150 B2
(45) Date of Patent: May 10, 2016

(54) DENTAL RESTORATIVE MATERIALS BASED ON POLYMERIZABLE AZIDES AND ALKYNES

(71) Applicant: Ivoclar Vivadent AG, Schaan (LI)

(72) Inventors: Norbert Moszner, Mauren (LI); Peter Burtscher, Rankweil (AT); Urs Karl Fischer, Arbon (CH); Thomas Hirt, Rebstein (CH); Ulrich S. Schubert, Jena (DE); Martin Hager, Jena (DE); Bobby Happ, Jena (DE); Benedict Sandmann, Jena (DE)

(73) Assignee: Ivoclar Vivadent AG, Schaan (LI)

( * ) Notice: Subject to any disclaimer, the term of this patent is extended or adjusted under 35 U.S.C. 154(b) by 143 days.

(21) Appl. No.: 14/100,207

(22) Filed: Dec. 9, 2013

(65) Prior Publication Data

US 2014/0171536 A1    Jun. 19, 2014

(30) Foreign Application Priority Data

Dec. 14, 2012    (EP) .................................... 12197372

(51) Int. Cl.
*A61K 6/08* (2006.01)
*A61K 6/087* (2006.01)
*C07D 403/14* (2006.01)

(52) U.S. Cl.
CPC .............. *A61K 6/087* (2013.01); *C07D 403/14* (2013.01)

(58) Field of Classification Search
CPC ............................. A61K 6/087; C09D 403/14
See application file for complete search history.

(56) References Cited

U.S. PATENT DOCUMENTS 8,557,888 B2    10/2013    Moszner et al.
2009/0220607 A1*    9/2009    Kiser et al. .................... 424/487

FOREIGN PATENT DOCUMENTS

EP    2455059 A1    5/2012

OTHER PUBLICATIONS

Lutz, F., et al., A classification and evaluation of composite resin systems, Journal of Prosthetic Dentistry, Oct. 1983, vol. 50, No. 4, pp. 480-488.
Viohl, J., et al., Die Chemie zahnärztlicher Füllungskunststoffe, Carl Hanser Verlag, Munich-Vienna, 1986, pp. 21-27.
Peutzfeldt, A., Resin composites in dentistry: the monomer systems, European Journal of Oral Sciences, 1997, vol. 105, pp. 97-116.
Nicholson, J. W., et al., The Chemistry of Modern Dental Filling Materials, Journal of Chemical Education, Nov. 1999, vol. 76, No. 11, pp. 1497-1501.
Stansbury, J. W., Curing Dental Resins and Composites by Photopolymerization, J. Esthet. Dent.,, 2000, vol. 12, pp. 300-308.
Moszner, N., et al., New Polymer-Chemical Developments in Clinical Dental Polymer Materials: Enamel-Dentin Adhesives and Restorative Composites, J. Polym. Sci. Part A: Polym. Chem., Aug. 6, 2012, vol. 50, pp. 4369-4402.
Abu-Orabi, S. T., et al., Reaction of Acetylenedicarboxaldehyde Bis(diethyl acetal) with Bis(azidomethyl)benzene, J. Chem. Eng. Data, 1986, vol. 31, No. 3, pp. 379-380.
Lutz, J.F., 1,3-Dipolar Cycloadditions of Azides and Alkynes: A Universal Ligation Tool in Polymer and Materials Science, Agnew. Chem. Int. Ed., 2007, vol. 46, pp. 1018-1025.
Banert, K., et al., The Exciting Chemistry of Tetraazidomethane, Agnew. Chem. Int. Ed., 2007, vol. 46, pp. 1168-1171.

* cited by examiner

*Primary Examiner* — Sanza McClendon
(74) *Attorney, Agent, or Firm* — Ann M. Knab; Thad McMurray

(57) ABSTRACT

The invention relates to a dental restorative material on the basis of at least one compound of Formula I A-[X-Q-(Y-CG)$_n$]$_m$    Formula I, wherein CG represents in each case independently an azide group N$_3$ or an alkyne group selected from the group consisting of —CR$^1$R$^2$—C≡CH,

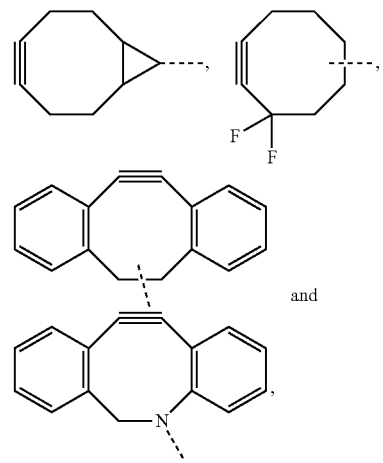

and with the proviso that the dental restorative material comprises at least one compound of Formula I comprising an azide group and at least one compound of Formula I comprising an alkyne group.
The invention also relates to the use of the dental restorative materials according to the invention for preparing dental composites, preferably composite blanks, which are suitable in particular for mechanical processing by means of computer-aided processing techniques such as milling and grinding processes, and which are suitable above all for preparing dental restoration materials such as inlays, onlays, crowns, bridges or veneering materials.

23 Claims, 2 Drawing Sheets

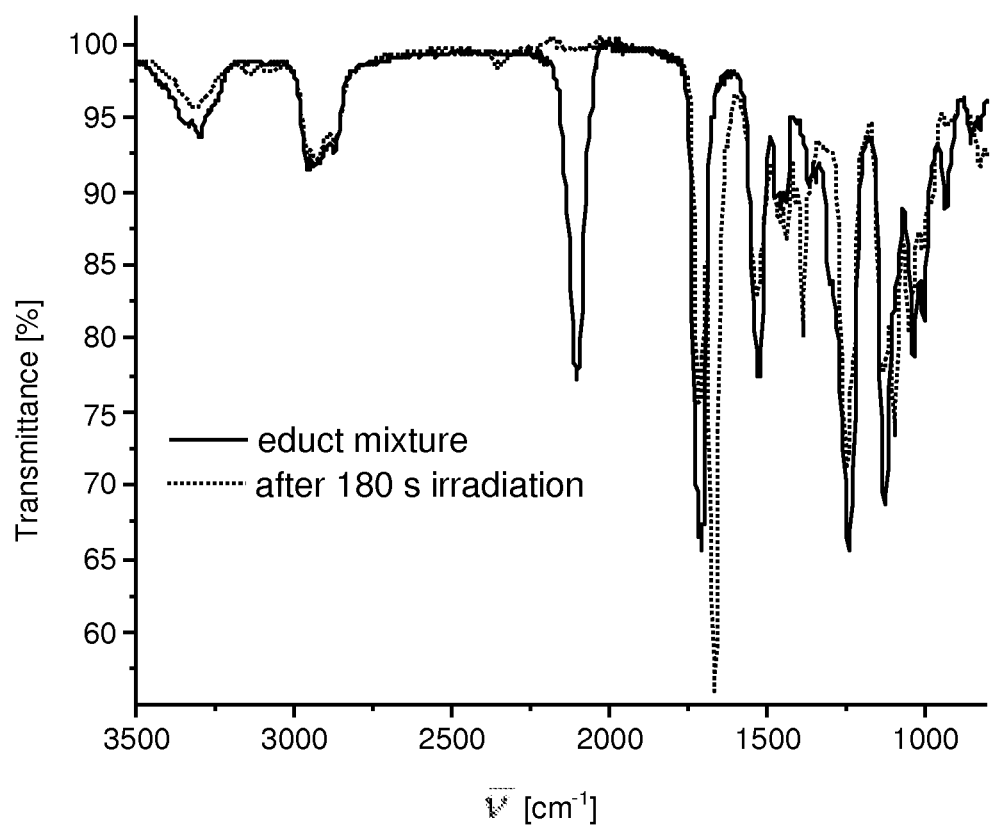

DENTAL RESTORATIVE MATERIALS BASED ON POLYMERIZABLE AZIDES AND ALKYNES

CROSS-REFERENCE TO RELATED APPLICATIONS

This application claims priority to European patent application No. 12197372.1 filed on Dec. 14, 2012, the disclosure of which is incorporated herein by reference in its entirety.

The present invention relates to thermally- and/or light-curing dental restorative materials, and in particular to dental composite materials with excellent mechanical properties for the preparation of dental composites for inlays, onlays, crowns, bridges or veneering materials.

Dental composites which e.g. are used as direct filling material, inlay, onlay, crowns or veneering material generally consist of a polymerizable organic matrix and of one or more fillers. Depending on the type of fillers, the monomer matrix and the application, the fill level can vary between approx. 50-90 wt.-%. According to the particle size and composition of the fillers, the composites are typically divided into macrofiller composites, homogeneous and heterogeneous microfiller composites, and hybrid composites (F. Lutz, R. W. Phillips, A classification and evaluation of composite resin systems, J. Prosthet. Dent. 50 (1983) 480-488).

The polymerizable organic matrix typically consists primarily of a mixture of monomers, initiator components, stabilizers and pigments (J. Viohl, K. Dermann, D. Quast, S. Venz, Die Chemie zahnärztlicher Füllungskunststoffe, Carl Hanser Verlag, Munich-Vienna 1986, 21-27). Mixtures of dimethacrylates are usually used as resins (cf. A. Peutzfeldt, Resin composites in dentistry: the monomer systems, Eur. J. Oral. Sci. 105 (1997) 97-116; J. W. Nicolson, H. M. Anstice, The chemistry of modern dental filling materials, J. Chem. Ed. 76 (1999) 1497-1501; J. W. Stansburry, Curing dental resins and composites by photopolymerization, J. Esthet. Dent., 12 (2000) 300-308; N. Moszner, T. Hirt, New Polymer-Chemical Developments in Clinical Dental Polymer Materials: Enamel-Dentin Adhesives and Restorative Composites, J. Polym. Sci. Part A: Polym. Chem. 50 (2012) 4369-4402). Examples of this are the highly viscous dimethacrylates 2,2-bis[4-(2-hydroxy-3-methacryloyloxypropyl)-phenyl]propane (Bis-GMA) and 1,6-bis-[2-methacryloyloxyethoxycarbonylamino]-2,4,4-trimethylhexane (UDMA) and the less viscous dimethacrylates used as diluting monomers such as bismethacryloyloxymethyl-tricyclo[5.2.1]decane (TCDMA), decanediol-1,10-dimethacrylate ($D_3MA$) and triethylene glycol dimethacrylate (TEGDMA).

The known dimethacrylate-based dental composites can be cured by thermal, redox-initiated or light-induced radical polymerization using suitable initiators. However, it has proved to be a disadvantage of these composites that a polymer network in which filler particles are firmly integrated usually already forms within seconds and with a correspondingly low monomer conversion at the so-called gel point. Even at almost complete monomer conversion, the final 3-dimensional polymer network contains numerous unconverted double bonds. The cross-linking densities which can be attained with the known dimethacrylate-based dental composites, and thus also the mechanical properties which can be achieved, are therefore severely limited.

It is therefore an object of the invention to provide dental restorative materials which are characterized by higher conversion of the polyreactive groups, improved mechanical properties, and above all by an increased modulus of elasticity, and which are suitable in particular for preparing dental composites for inlays, onlays, crowns, bridges or veneering materials.

This object is achieved according to the invention by a dental restorative material on the basis of at least one compound of Formula I

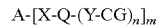  Formula I, wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical such as alkylene-cyclyl radical, cyclyl-alkylene radical, cyclyl-alkylene-cyclyl radical or alkylene-cyclyl-alkylene-cyclyl-alkylene radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, in particular selected from $C_1$-$C_5$ alkyl, OH, $OCH_3$ and $OCOCH_3$, CG represents in each case independently an azide group $N_3$ or an alkyne group selected from the group consisting of —$CR^1R^2$—C≡CH,

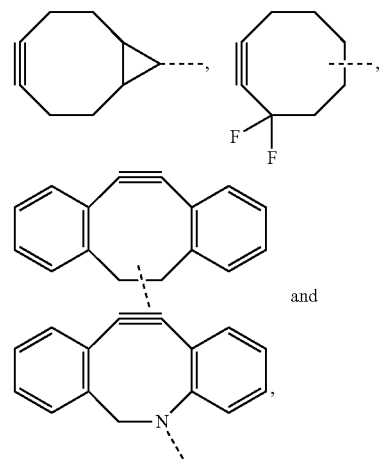

with the proviso that the dental restorative material comprises at least one compound of Formula I comprising an azide group and at least one compound of Formula I comprising an alkyne group, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, in particular selected from $CH_3$, $C_2H_5$, OH, $OCH_3$ and $OCOCH_3$, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4.

The indication that a radical can be interrupted by a group, such as for example —O—, is to be understood such that the group is inserted into the carbon chain of the radical, i.e. is bordered on both sides by carbon atoms. The number of these groups is therefore smaller than the number of carbon atoms by at least 1 and the groups cannot be terminal. According to the invention, radicals which are not interrupted by the indicated groups are preferred.

According to the invention, only those compounds which are compatible with the chemical valence theory are considered.

Those compounds of Formula I are particularly preferred in which in each case independently of each other A represents —N= or an m-valent alkylene radical, cycloalkylene radical, heterocycloalkylene radical, arylene radical, heteroarylene radical, mixed alkylene-cyclyl radical such as alkylene-cyclyl radical, cyclyl-alkylene radical, cyclyl-alkylene-cyclyl radical or alkylene-cyclyl-alkylene-cyclyl-alkylene radical or cyclyl-O-cyclyl radical, wherein alkylene represents in each case independently a linear or branched aliphatic $C_1$-$C_{20}$ radical which can be interrupted by one or more —O—, —S—, —CO—O—, —O—CO— or —O—CO—O—, cycloalkylene represents in each case independently a cycloaliphatic $C_3$-$C_{12}$ radical, heterocycloalkylene represents in each case independently a heterocycloaliphatic $C_3$-$C_{12}$ radical, arylene represents in each case independently an aromatic $C_6$-$C_{12}$ radical, heteroarylene represents in each case independently a heteroaromatic $C_3$-$C_{12}$ radical, cyclyl represents in each case independently cycloalkylene, heterocycloalkylene, arylene or heteroarylene and the indicated radicals can in each case independently carry one or more substituents, in particular selected from $C_1$-$C_3$ alkyl, $OCH_3$ and $OCOCH_3$, CG represents in each case independently an azide group $N_3$ or an alkyne group selected from the group consisting of —$CR^1R^2$—C≡CH,

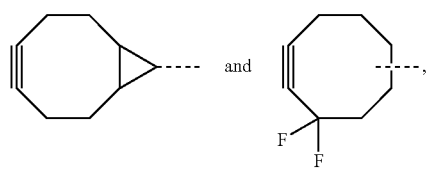

Q in each case independently is missing or represents an (n+1)-valent linear or branched aliphatic $C_1$-$C_{10}$ alkylene radical which can be interrupted by one or more —O— or —S—, or a phenylene radical, wherein the indicated radicals in each case independently can carry one or more substituents, in particular selected from $CH_3$, $C_2H_5$, $OCH_3$ and $OCOCH_3$, $R^1$, $R^2$ and $R^3$ in each case independently represent H or a $C_1$-$C_5$ alkyl radical and in particular a $C_1$-$C_3$ alkyl radical, X and Y in each case independently are missing or represent —O—, —S—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2, 3 or 4, n in each case independently can assume the values 1, 2 or 3, and in particular 1 or 2, and most preferably is 1.

Compounds are particularly preferred in which all variables have one of the above-defined meanings and in particular one of the preferred meanings.

According to the invention, dental restorative materials are particularly preferred which comprise at least one azide of Formula IA $$A\text{-}[X\text{-}Q\text{-}(Y\text{-}CG)_n]_m \qquad \text{Formula IA}$$

wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical such as alkylene-cyclyl radical, cyclyl-alkylene radical, cyclyl-alkylene-cyclyl radical or alkylene-cyclyl-alkylene-cyclyl-alkylene radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, in particular selected from $C_1$-$C_5$ alkyl, OH, $OCH_3$ and $OCOCH_3$, CG in each case independently represents an azide group $N_3$, Q in each case independently is missing or represents an (n+1)-valent linear or branched aliphatic $C_1$-$C_{10}$ alkylene radical which can be interrupted by one or more —O— or —S—, or a phenylene radical, wherein the indicated radicals in each case independently can carry one or more substituents, in particular selected from $CH_3$, $C_2H_5$, $OCH_3$ and $OCOCH_3$, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and at least one alkyne of Formula IB $$A\text{-}[X\text{-}Q\text{-}(Y\text{-}CG)_n]_m \qquad \text{Formula IB,}$$

wherein
A represents —O—, —N═, —NR³—, ═N—N═, —NR³—N═, ═N—NR³—, —NR³—NR³— or an m-valent alkylene radical, cycloalkylene radical, heterocycloalkylene radical, arylene radical, heteroarylene radical, mixed alkylene-cyclyl radical such as alkylene-cyclyl radical, cyclyl-alkylene radical, cyclyl-alkylene-cyclyl radical or alkylene-cyclyl-alkylene-cyclyl-alkylene radical or cyclyl-O-cyclyl radical, wherein
  alkylene represents in each case independently a linear or branched aliphatic $C_1$-$C_{50}$ radical which can be interrupted by one or more —O—, —S—, —NR³—, —CO—O—, —O—CO—, —O—CO—O—, —CO—NR³—, —NR³—CO—, —O—CO—NR³—, —NR³—CO—O— or —NR³—CO—NR³—,
  cycloalkylene represents in each case independently a cycloaliphatic $C_3$-$C_{18}$ radical,
  heterocycloalkylene represents in each case independently a heterocycloaliphatic $C_3$-$C_{18}$ radical,
  arylene represents in each case independently an aromatic $C_6$-$C_{18}$ radical,
  heteroarylene represents in each case independently a heteroaromatic $C_3$-$C_{18}$ radical,
  cyclyl represents in each case independently cycloalkylene, heterocycloalkylene, arylene or heteroarylene and the indicated radicals in each case independently can carry one or more substituents, in particular selected from $C_1$-$C_5$ alkyl, OH, OCH₃ and OCOCH₃,
CG represents in each case independently an alkyne group selected from the group consisting of —CR¹R²—C≡CH,

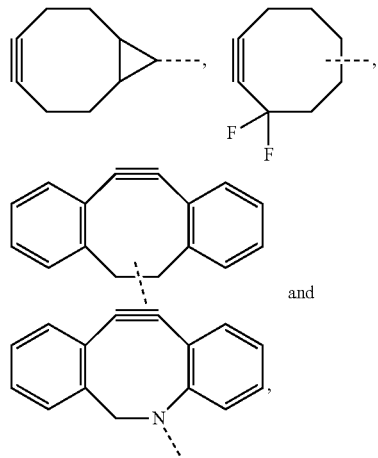

and

Q in each case independently is missing or represents an (n+1)-valent linear or branched aliphatic $C_1$-$C_{10}$ alkylene radical which can be interrupted by one or more —O— or —S—, or a phenylene radical, wherein the indicated radicals in each case independently can carry one or more substituents, in particular selected from CH₃, C₂H₅, OCH₃ and OCOCH₃,
R¹, R² and R³ in each case independently represent H or a $C_1$-$C_{10}$ alkyl radical,
X and Y in each case independently are missing or represent —O—, —S—, —NR³—, —CO—, —CO—O—, —O—CO—, —O—CO—O—, —CO—NR³—, —NR³—CO—, —O—CO—NR³—, —NR³—CO—O— or —NR³—CO—NR³—,
m in each case independently can assume the values 2 to 6 and
n in each case independently can assume the values 1 to 4.

Those compounds of Formula IA and IB are particularly preferred in which in each case independently of each other one or more of the variables have one of the preferred meanings defined above for Formula I. Compounds are particularly preferred in which all variables have one of the above-defined meanings and in particular one of the preferred meanings.

Moreover, dental restorative materials are preferred in which alkyne groups and azide groups are present entirely or approximately in stoichiometric ratio, and in particular in a ratio of 2:1-1:2, preferably in a ratio of 1.5:1-1:1.5, particularly preferably in a ratio of 1.1:1-1:1.1 and most preferably in a ratio of 1.05:1-1:1.05.

Those dental restorative materials are further preferred in which the compounds of Formula I have an average functionality of >2.2 and in particular >2.5. The average functionality refers to the average number of groups CG based on the molecules of compounds of Formula I contained in the dental restorative material.

BRIEF DESCRIPTION OF THE FIGURES

Further advantages, details and features emerge from the following description of embodiments of the invention on the basis of the drawings, in which:
FIG. 3 shows an ATR-IR spectrum of a cross-linked polymer obtained according to the invention.

Figure 1:
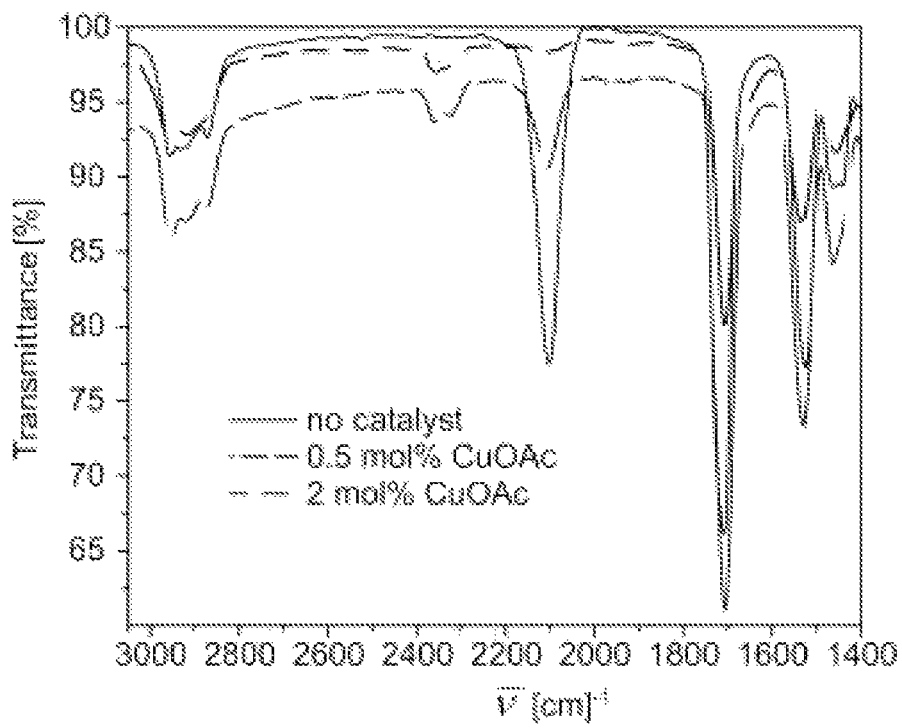
FIG. 1 shows AT-IR spectra of products obtained according to the invention.

It was surprisingly found that the dental restorative materials according to the invention, which comprise at least one compound of Formula I, and in particular at least one azide of Formula IA and at least one alkyne of Formula IB, are excellently polymerizable and display a very high conversion of the polyreactive groups, and after curing have improved mechanical properties such as a much higher modulus of elasticity.

Moreover, it has been shown that, based on the dental restorative materials according to the invention, polymer networks with customized properties can be prepared by suitable selection of the compounds of Formula I, and in particular of the multifunctional azides of Formula IA and the multifunctional alkynes of Formula IB, as well as by varying the average functionality of these compounds in the dental restorative material by setting a suitable mixture ratio in particular of the azides and alkynes. In this context, the network density increases with the average functionality of the compounds and the achieved conversion of the polymerizable groups. By varying the structure of the compounds of Formula I, such as for instance the use of flexible or rigid spacers for bonding the azide and alkyne groups, respectively, the properties of the obtained polycycloaddition networks can be influenced further. Moreover, the degree of conversion of the functional groups and thus the cross-linking density can be further increased by thermal post-treatment. Finally, the mechanical properties can be further improved by adding fillers. The dental restorative materials according to the invention based on compounds of Formula I are therefore suitable in particular for preparing dental restoration materials such as high-modulus composite milling blanks for CAD/CAM-based processing techniques for preparing tooth-colored inlays, onlays, bridges or crowns.

Compounds of Formula I can be prepared easily according to synthesis methods known per se. Azides of Formula IA can thus, for example, be obtained by nucleophilic substitution of suitable di- or higher-functionalized halides (Z=Cl,Br,I) or p-toluenesulphonic acid esters (Z=OTos) with sodium azide NaN₃:

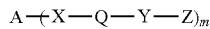

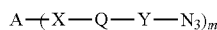

Specific Example

Reaction of 2,2,2-tri(chloromethyl)ethanol with Sodium Azide

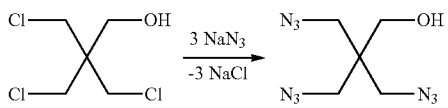

Furthermore, azide groups can be prepared in a manner known per se from aromatic hydrazines by diazotization, from alcohols by Mitsunobu reaction, or from isocyanates by addition of 2-azidoethanol.

Specific Example

Reaction of trimethyl hexamethylene diisocyanate with 2-azidoethanol or with 2-bromoethanol Followed by Sodium Azide

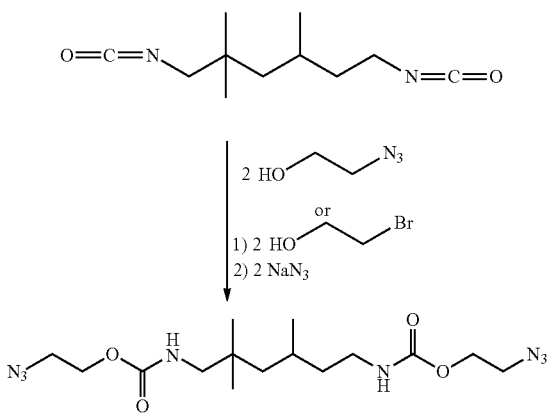

Alkynes of Formula IB can easily be obtained starting from commercially available monofunctional alkynes, such as propargylamine (Z=NH₂), propargylacetic acid (Z=CH₂COOH), propargyl alcohol (Z=OH) or propargyl halides (Z=Cl,Br), by reaction with suitable di- or higher-functionalized compounds such as di- or polyols:

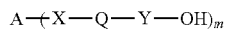

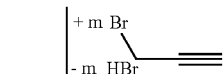

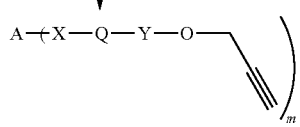

Specific Example

Reaction of tetra(hydroxymethyl)methane with Propargyl Bromide

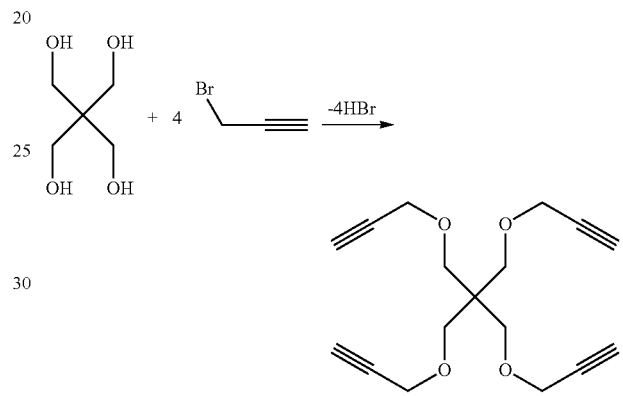

The synthesis of azides of Formula IB with cyclooctyne groups can, for example, be carried out by reacting bi- or higher-functional isocyanates with corresponding hydroxy cyclooctynes.

Specific Example

Reaction of trimethyl hexamethylene diisocyanate with bicyclo[6.1.0]non-4-yn-9-ol

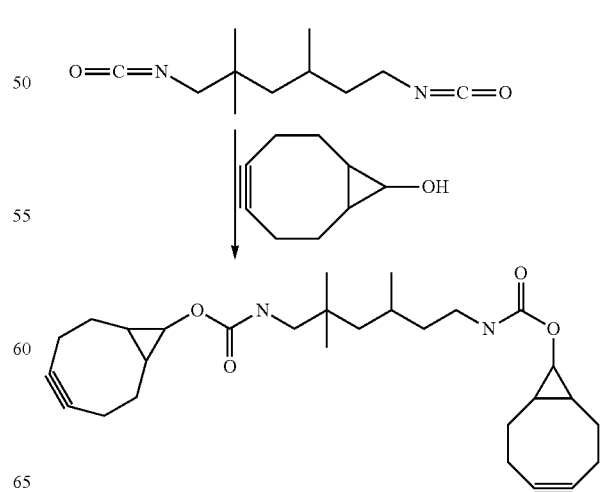

Examples of the compounds of Formula I according to the invention are:
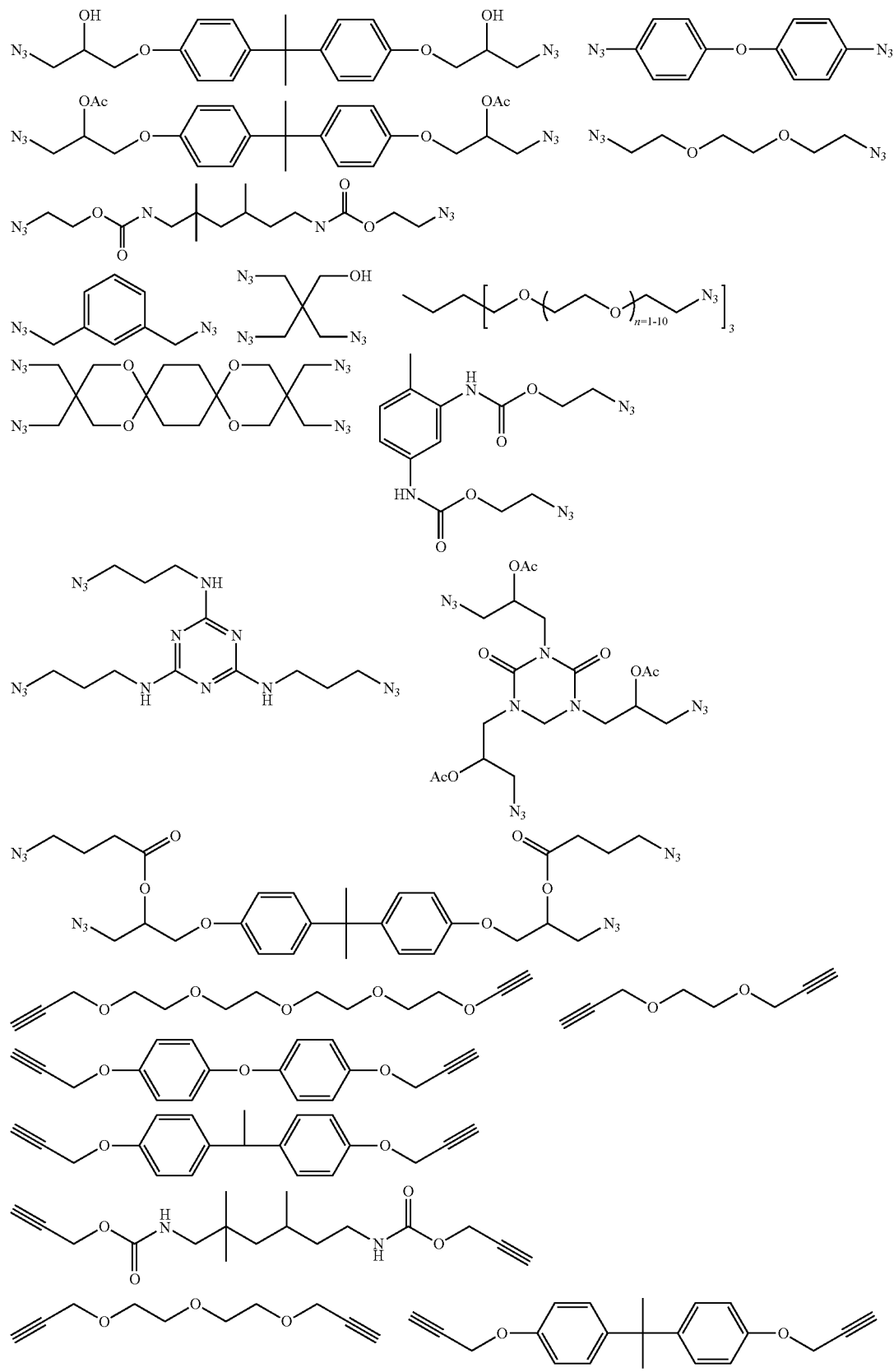

-continued
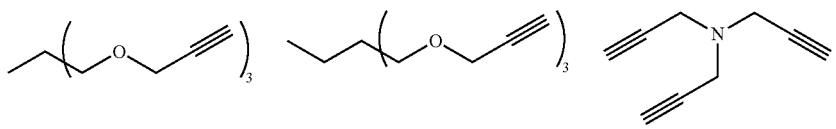
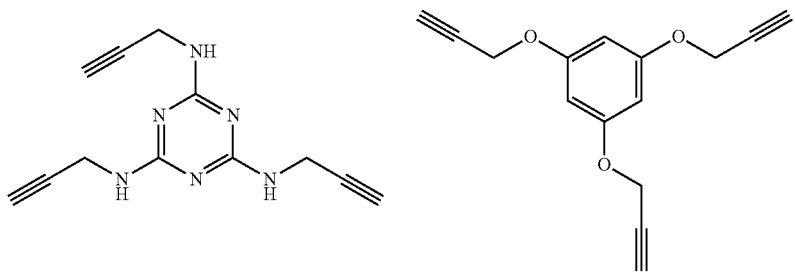
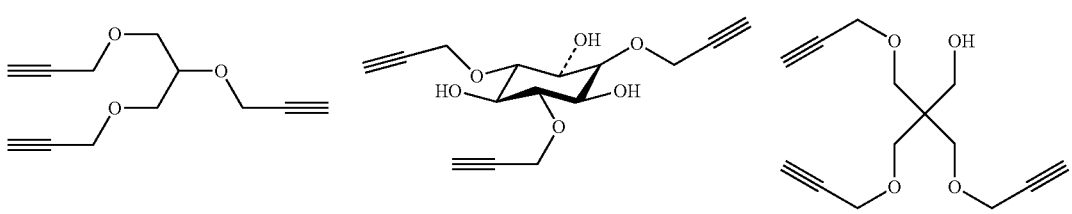
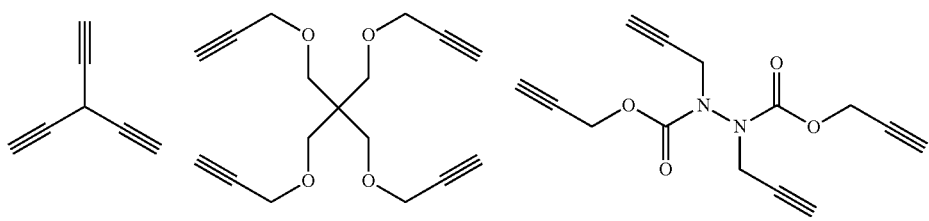
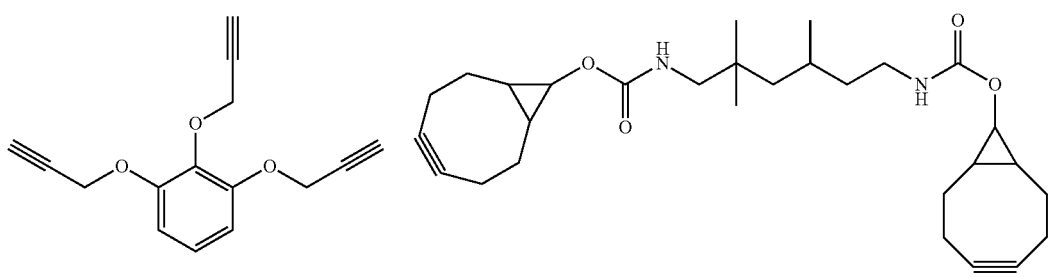
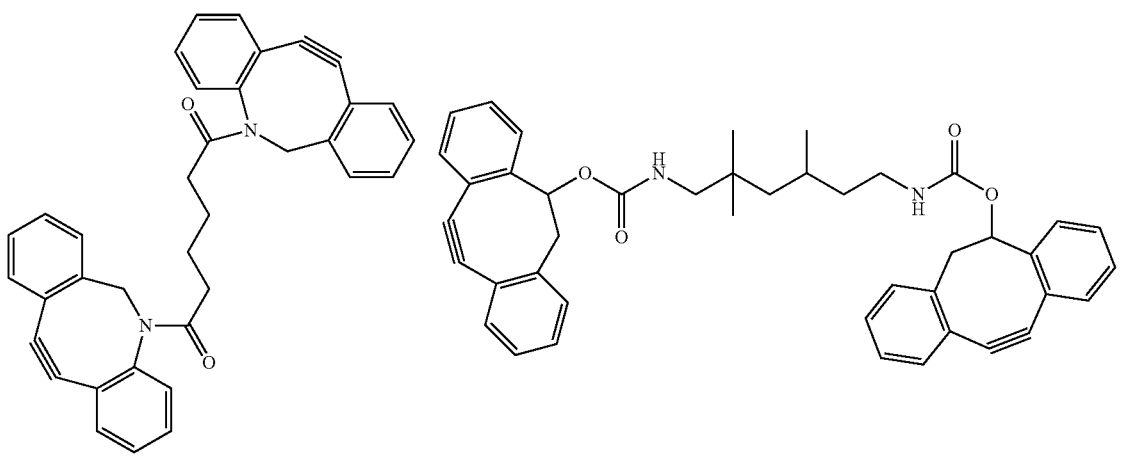

-continued

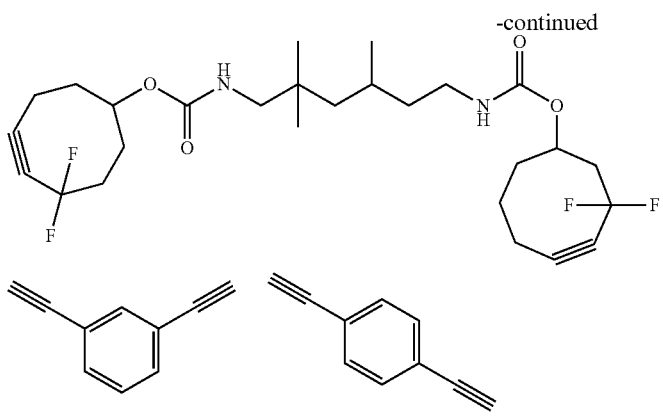
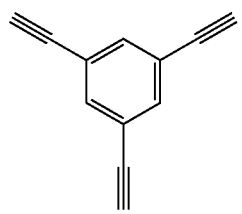

The dental restorative materials according to the invention preferably also comprise a catalyst for the azide-alkyne cycloaddition.

Suitable as thermal catalysts for the azide-alkyne cycloaddition are mainly copper, ruthenium, nickel, palladium and platinum compounds and complexes, and in particular copper (I), ruthenium(I), nickel(II), palladium(II) and platinum(II) compounds and complexes. Simple copper(I) salts such as CuCl, CuBr, CuI or CuOAc and copper(I) complexes such as CuOTf, $Cu(CH_3C(O)CHC(O)CH_3)$, $CuI.P(OEt)_3$, [Cu $(CH_3CN)_4]PF_6$ or $Cu(PPh_3)Br$ are particularly suitable. These can additionally be stabilized by means of chelating ligands such as tris-[(1-benzyl-1H-1,2,3-triazol-4-yl)methyl] amine (TBTA), N,N,N',N'',N''-pentamethyldiethylene-triamine (PMDETA), N,N,N'-trimethylethylenediamine (TRMEDA) or bathophenanthroline disulphonate (batho). Furthermore, mixtures of copper(II) salts with reducing agents can be used. Examples of suitable copper(II) salts are $CuSO_4$, $CuCl_2$, $CuBr_2$ and $CuI_2$. These can be converted into the corresponding Cu(I) species using, for example, ascorbic acid or its sodium salt. Alternatively, catalytic Cu(I) species can also be produced electrochemically from copper(II) salts. Further examples of suitable compounds are Cp*Ru $(PPh_3)_2Cl$, [Cp*RuCl]$_n$ and a mixture of $PtCl_2$ and PMDETA. CuOAc is particularly preferred. An exceptional catalyst activity can be achieved using a mixture of tripropargylamine and CuOAc, wherein the CuOAc is preferably used in a quantity of 0.15-0.25 mol %. The formation of the active catalyst species can be tracked by the color change from green to yellow occurring in the course of the reaction.

Suitable light-inducible catalysts for the azide-alkyne cycloaddition are mainly photoreducible copper(II) compounds as well as mixtures of copper(II) compounds with light-inducible reducing agents. Examples of suitable copper (II) compounds are $CuSO_4$, $CuCl_2$, $CuBr_2$, $Cu(OH)_2$, $Cu(OAc)_2$, CuO, $Cu(ClO_4)_2$ and $Cu(NO_3)_2$, as well as the hydrates and THF adducts thereof. Suitable light-inducible reducing agents, in particular for the UVA range (320-400 nm), are mainly Norrish type I photoinitiators such as benzophenone, 2-hydroxy-2-methyl-1-phenyl-1-propanone, 4-(2-hydroxyethoxy)phenyl-(2-hydroxy-2-propyl)ketone, bis-(2,6-dimethoxybenzoyl)-2,4,4-trimethylpentylphosphine oxide, bis-(2,4,6-trimethylbenzoyl)phenyl-phosphine oxide, 2,2-dimethoxy-2-phenylacetophenone, 2-benzyl-2-dimethylamino-4'-morpholinobutyrophenone (DBMP), 2,4, 6-(trimethyl-benzoyl)diphenylphosphine oxide (TMDPO) and diphenyliodonium hexafluorophosphate. Suitable light-inducible reducing agents, in particular for the visible range (400-800 nm), are mainly photoinitiators from the group of titanocenes, such as dicyclopentadienyl-bis-[2,6-difluoro-3-(1-pyrrolyl)phenyl]titanium, and of α-diketones, such as 9,10-phenanthrenequinone, 1-phenyl-propane-1,2-dione, diacetyl or camphorquinone. These light-inducible reducing agents can form blue light-induced catalytic Cu(I) species for the azide-alkyne cycloaddition for instance in combination with $CuCl_2$/PMDETA.

Photoinitiators as light-inducible reducing agents for the visible range additionally form polymerization-initiating radicals on irradiation, optionally in the presence of coinitiators. Examples of this are mixtures of camphorquinone with tertiary amines, in particular tertiary aromatic amines. N,N-Dialkylanilines such as N,N-dimethylaniline, N,N-dialkyl-p-toluidines such as N-dimethyl-p-toluidine, N,N-dialkyl-3,5-xylidines such as N,N,3,5-tetramethyl-aniline, p-(N,N-dialkylamino)phenylethanols, p-(N,N-dialkylamino)-benzoic acid derivatives such as p-(dimethylamino) benzonitrile, p-(N,N-dialkylamino)benzaldehydes such as N,N-dimethylamino-p-benzaldehyde, p-(N,N-dialkylamino) phenylacetic acid esters such as p-(dimethylamino)benzoic acid ethyl ester or p-(N,N-dialkyl-amino)phenylpropanoic acid esters are particularly suitable tertiary aromatic amines. Tertiary aliphatic amines such as tri-n-butylamine, dimethylaminoethan-2-ol, triethanolamine, dimethylamino-ethyl methacrylate or N,N-dimethylbenzylamine are also suitable.

If substituted cycloalkynes such as difluorinated cyclooctynes are used, the use of catalysts can often be dispensed with, as in this case the azide-alkyne cycloaddition is accompanied by a reduction in the ring strain.

Hybrid materials which, in addition to at least one compound of Formula I, and in particular at least one azide of Formula IA and at least one alkyne of Formula IB, comprise radically polymerizable monomers are also particularly suitable. Such hybrid materials can be cured in steps (first thermally- and then light-induced) or at the same time (light-induced) by catalyst combinations of copper(I) or copper(II) compounds with radical photoinitiators as light-inducible reducing agents.

In particular, mono- or polyfunctional (meth)acrylic acid derivatives are suitable as radically polymerizable monomers (co-monomers). By monofunctional (meth)acrylic acid derivatives are meant compounds with one (meth)acrylic acid group, by polyfunctional (meth)acrylic acid derivatives are meant compounds with two or more, preferably 2 to 4, (meth) acrylic acid groups. Polyfunctional monomers have a cross-linking effect.

Mono- or polyfunctional (meth)acrylic acid derivatives which are preferred according to the invention are methyl-, ethyl-, hydroxyethyl-, butyl-, benzyl-, tetrahydrofurfuryl- or isobornyl-(meth)acrylate, p-cumyl-phenoxyethylene glycol methacrylate (CMP-1E), bisphenol-A-di(meth)acrylate, Bis-GMA (an addition product of methacrylic acid and bisphenol-A-diglycidyl ether), ethoxylated or propoxylated bisphenol-A-dimethacrylate, such as e.g. the bisphenol-A-dimethacrylate SR-348c (Sartomer) with 3 ethoxy groups or 2,2-bis[4-(2-methacryloxy propoxy)phenyl]propane, UDMA (an addition product of 2-hydroxyethyl methacrylate (HEMA) and 2,2,4-trimethyl-hexamethylene diisocyanate), di-, tri- or tetraethylene glycol di(meth)acrylate, trimethylolpropane tri(meth)acrylate, pentaerythritol tetra(meth)acrylate, glycerol di- and tri(meth)acrylate, 1,4-butanediol di(meth)acrylate, 1,10-decanediol di(meth)acrylate ($D_3MA$) and 1,12-dodecanediol di(meth)acrylate.

Particularly preferred mono- or polyfunctional (meth) acrylic acid derivatives are N-mono- or -disubstituted acrylamides, such as N-ethylacrylamide, N,N-dimethacrylamide, N-(2-hydroxyethyl)acrylamide or N-methyl-N-(2-hydroxyethyl)acrylamide, N-monosubstituted methacrylamides such as N-ethylmethacrylamide or N-(2-hydroxy-ethyl)methacrylamide as well as N-vinylpyrrolidone and allyl ether. These monomers are characterized by high hydrolysis stability and are particularly suitable as diluting monomers because of their relatively low viscosity.

Preferred polyfunctional (meth)acrylic acid derivatives with high hydrolysis stability are cross-linking pyrrolidones, such as 1,6-bis(3-vinyl-2-pyrrolidonyl)-hexane, bisacrylamides such as methylene or ethylene bisacrylamide and bis(meth)acrylamides such as N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized by conversion from the corresponding diamines with (meth)acrylic acid chloride.

Preferably, mixtures of the above-mentioned monomers are used.

In addition to at least one compound of Formula I, and in particular at least one compound of Formula IA and at least one compound of Formula IB, and optionally the above-mentioned co-monomers, the dental restorative materials according to the invention can preferably also comprise additional radically polymerizable, acid group-containing monomers (adhesive monomers). Preferred acid groups are carboxylic acid groups, phosphonic acid groups, phosphoric acid groups and sulphonic acid groups.

Preferred monomers with polymerizable carboxylic acids are maleic acid, acrylic acid, methacrylic acid, 2-(hydroxymethyl)acrylic acid, 4-(meth)acryloyloxyethyltrimellitic anhydride, 10-methacryloyloxy-decylmalonic acid, N-(2-hydroxy-3-methacryloyloxypropyl)-N-phenyl-glycine and 4-vinylbenzoic acid.

Preferred monomers with polymerizable phosphonic acid groups are vinyl phosphonic acid, 4-vinylphenyl phosphonic acid, 4-vinyl-benzyl phosphonic acid, 2-methacryloyloxyethyl phosphonic acid, 2-methacrylamidoethyl phosphonic acid, 4-methacrylamido-4-methyl-pentyl phosphonic acid, 2-[4-(dihydroxyphosphoryl)-2-oxa-butyl]-acrylic acid, 2-[4-(dihydroxyphosphoryl)-2-oxa-butyl]-acrylic acid ethyl and 2,4,6-trimethylphenyl ester.

Preferred monomers with polymerizable phosphoric acid groups are 2-methacryloyloxypropyl mono- or dihydrogen phosphate, 2-methacryloyloxyethyl mono- or dihydrogen phosphate, 2-methacryloyloxyethyl-phenyl hydrogen phosphate, dipentaerythritol-pentamethacryloyloxy-phosphate, 10-methacryloyloxydecyl dihydrogen phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propan-2-yl-dihydrogen phosphate.

Preferred monomers with polymerizable sulphonic acid groups are vinylsulphonic acid, 4-vinylphenylsulphonic acid and 3-(methacrylamido)propylsulphonic acid.

The compositions according to the invention furthermore preferably also comprise organic or inorganic filler particles to improve the mechanical properties or to adjust the viscosity.

Preferred inorganic particulate fillers are amorphous spherical materials based on oxides, such as $ZrO_2$ and $TiO_2$, or mixed oxides of $SiO_2$, $ZrO_2$ and/or $TiO_2$ with an average particle size of from 0.005 to 2 µm, preferably 0.1 to 1 µm, nanoparticulate or microfine fillers such as pyrogenic silicic acid or precipitated silicic acid with an average particle size of from 5 to 200 nm, preferably 10 to 100 nm, minifillers such as quartz, glass ceramic or glass powders, for example from barium or strontium aluminium silicate glasses, with an average particle size of from 0.01 to 15 µm, preferably 0.1 to 1 µm, as well as radiopaque fillers such as ytterbium trifluoride or nanoparticulate tantalum(V) oxide or barium sulphate or mixed oxides of $SiO_2$ with ytterbium(III) oxide or tantalum(V) oxide with an average particle size of from 10 to 1000 nm, preferably 100 to 300 nm. The average particle size can in particular be determined by transmission or scanning electron microscopy or by laser diffraction. Preferably, transmission electron microscopy can be used in the range of from 1 nm to 50 nm, scanning electron microscopy can be used in the range of from 50 nm to 1 µm, and laser diffraction can be used in the range of from 1 µm to 100 µm to determine the average particle size. Fibrous fillers, nanofibres or whiskers are also suitable.

To improve the bonding between the filler particles and the polycycloaddition matrix, in particular fillers based on $SiO_2$ can be surface modified with azide- or alkyne-functionalized silanes. Examples of such silanes are 3-azidopropyltriethoxysilane and N-[3-(triethoxysilyl)propyl]carbamic acid propargyl ester. To modify the surface of non-silicate fillers, for example based on $ZrO_2$ or $TiO_2$, functionalized acid phosphates such as propargyl dihydrogen phosphate can also be used.

Moreover, the dental restorative materials according to the invention can comprise further additives, in particular stabilizers, flavorings, colorants, microbiocidal active ingredients, fluoride ion-releasing additives, optical brighteners, plasticizers, UV absorbers or solvents such as water or ethanol or corresponding solvent mixtures.

Particularly preferred are dental restorative materials based on at least one compound of Formula I, and in particular at least one azide of Formula IA and at least one alkyne of Formula IB, which comprise the following components:
a) 0.1 to 80 wt.-%, in particular 1 to 60 wt.-%, preferably 5 to 50 wt.-% and particularly preferably 10 to 40 wt.-% of at least one compound of Formula I, and preferably a mixture of at least one azide of Formula IA and at least one alkyne of Formula IB,
b) 0.01 to 10 wt.-%, preferably 0.1 to 3 wt.-% and particularly preferably 0.2 to 2 wt.-% catalyst,
c) 0 to 80 wt.-%, preferably 1 to 60 wt.-% and particularly preferably 5 to 50 wt.-% co-monomer,
d) 0 to 90 wt.-%, preferably 10 to 80 wt.-% and particularly preferably 20 to 70 wt.-% filler and
e) 0 to 70 wt.-%, preferably 1 to 50 wt.-% and particularly preferably 5 to 20 wt.-% solvent.

The invention also relates to the use of the dental restorative materials according to the invention for preparing dental composites, preferably composite blanks, which are suitable in particular for mechanical processing by means of computer-aided processing techniques such as milling and grinding processes, and which are suitable above all for preparing dental restoration materials such as inlays, onlays, crowns, bridges or veneering materials.

Furthermore, the invention also relates to the use of at least one compound of Formula I, and in particular at least one azide of Formula IA and at least one alkyne of Formula IB, as described above for preparing a dental restorative material and in particular a dental composite material.

The invention is explained in more detail below by means of examples.

EXAMPLES

Example 1

Synthesis of 1,2-bis-(2-azidoethoxy)ethane

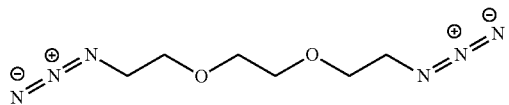 [SMILES: [N-]=[N+]=NCCOCCOCCN=[N+]=[N-]]

Sodium azide (4.25 g, 65.4 mmol, 3 eq.) was added to a solution of triethylene glycol-bis-(4-toluenesulphonate) (10 g, 21.8 mmol) in DMSO (130 ml). The reaction mixture was stirred for 48 h at room temperature and then the reaction was stopped by addition of water (100 ml). The reaction product was extracted with diethyl ether (3×50 ml) and the combined organic phases were washed with water (3×50 ml). The organic phase was dried with anhydrous $MgSO_4$. After removal of the solvent under reduced pressure, 4.32 g (98% yield) of the product was obtained as a yellow oil.

$^1$H-NMR (300 MHz, $CDCl_3$): δ=3.70-3.66 (m, 8H), 3.38 (t, J=5 Hz, 4H).

$^{13}$C-NMR (75 MHz, $CDCl_3$): δ=70.7, 70.1, 50.7.

Analysis: calculated for $C_6H_{42}N_6O_2$: C, 36.00%; H, 6.04%; N, 41.98%. found: C, 36.25%; H, 5.79%; N, 42.08%.

Example 2

Synthesis of 1,6-bis-(prop-2-yn-oxycarbonylamino)-2,2,4-trimethylhexane

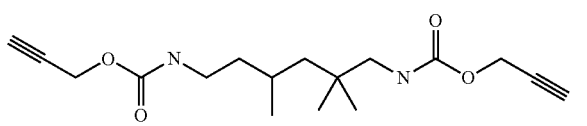 [SMILES: C#CCOC(=O)NCCC(C)CC(C)(C)CNC(=O)OCC#C]

Propargyl alcohol (2.67 g, 47.6 mmol, 2 eq.) was slowly added dropwise to a solution of 2,2,4-trimethylhexane-1,6-diisocyanate (5 g, 23.8 mmol, diastereomer mixture) and dibutyltin(II) dilaurate (6 mg, 9.52 μmol, 0.0004 eq.) in toluene (10 ml) over a period of 15 min and the reaction mixture was stirred for 48 h at 60° C. After filtration over a short silica column, the solvent was removed under reduced pressure. 7.51 g (98% yield) of the product was obtained as a viscous yellow oil.

$^1$H-NMR (300 MHz, $CDCl_3$): δ=5.14-4.91 (br, 2H, N—H), 4.65 (br, 4H, C(O)O—$CH_2$), 3.20-2.88 (m, 4H, NH—$CH_2$), 2.46 (d, J=1.8 Hz, 2H, C≡CH), 1.70-1.22 (br, 3H), 1.05-0.86 (m, 11H, $CH_2$, $CH_3$).

$^{13}$C-NMR (75 MHz, $CDCl_3$): δ=155.8, 155.7, 155.4, 129.0, 128.2, 125.3, 78.4, 74.6, 74.5, 52.5, 52.3, 51.4, 48.6, 46.4, 45.9, 41.9, 39.2, 39.1, 37.4, 35.0, 32.9, 29.4, 27.4, 26.1, 25.5, 25.1, 22.3, 21.4, 20.5.

ESI-MS (m/z (%)): 345.18 (100) [M++Na].

Analysis: calculated for $C_{17}H_{26}N_2O_4$: C, 63.33%; H, 8.13%; N, 8.69%. found: C, 63.07%; H, 7.91%; N, 8.83%.

Example 3

General Procedure for Thermal Cu(I)-Catalyzed Azide-Alkyne Cyclopolyadditions

A stoichiometric mixture of azide and alkyne compounds was weighed into a receptacle and stirred for 10 min. Then the copper(I) catalyst (0.1 to 5 mol %) was added and stirred for a further 5 min, until the catalyst dissolved, which typically led to a yellow coloration of the solution. The mixture was then placed into a metal or Teflon press sleeve (0.5-1.0 mm high, internal diameter 15 mm) and covered with PET film. The mixture was left to stand for 24 h at room temperature and then heated for 24 h to 32° C., as a result of which complete curing was achieved. The course of the reaction was tracked by means of IR spectroscopy by tracking the decline in IR absorption of the azide group at 2100 $cm^{-1}$.

Example 4

Thermal Cu(I)-Catalyzed Azide-Alkyne Cyclopolyaddition of 1,2-bis-(2-azidoethoxy)ethane and 1,6-bis-(prop-2-yn-oxycarbonylamino)-2,2,4-trimethylhexane

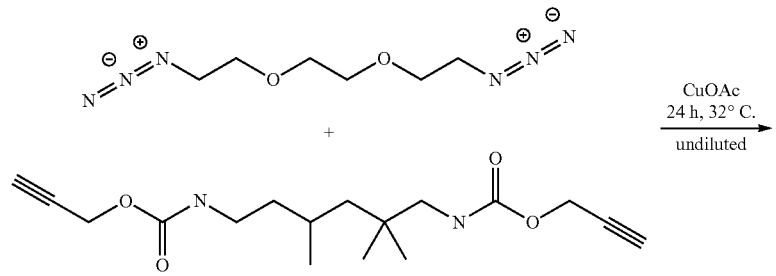

-continued

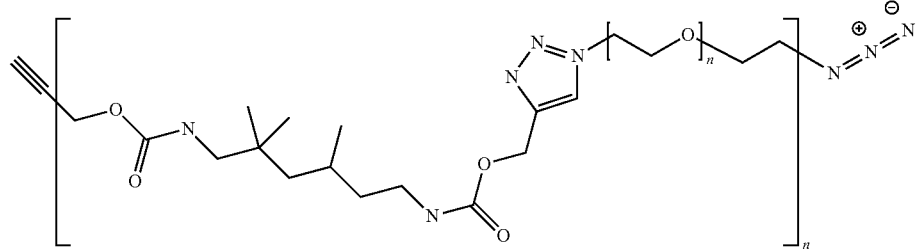

Stoichiometric quantities of 1,2-bis-(2-azidoethoxy) ethane from Example 1 and 1,6-bis-(prop-2-yn-oxycarbonylamino)-2,2,4-trimethylhexane from Example 2 were reacted in the presence of 0.5 mol % and 2 mol %, respectively, copper(I) acetate according to the above general procedure. AT-IR spectra of the obtained products are shown in FIG. 1.

Example 5

Thermal Cross-Linking Cu(I)-Catalyzed Polycycloaddition of a Mixture of 1,3-bis-(azidomethyl)benzene and tripropargylamine

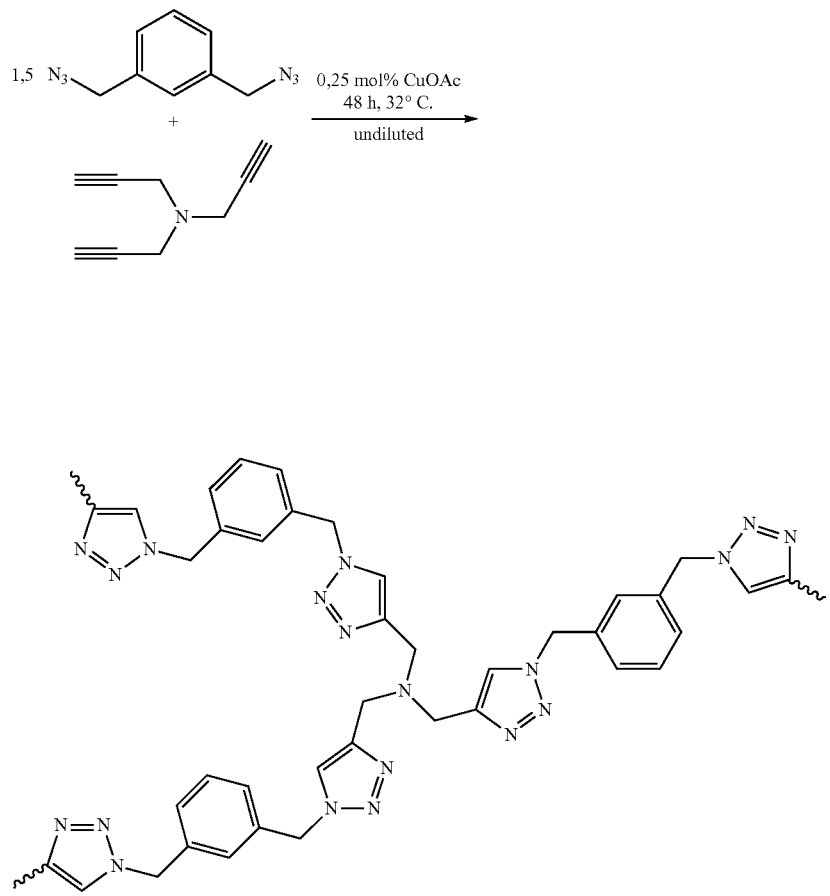

Figure 2:
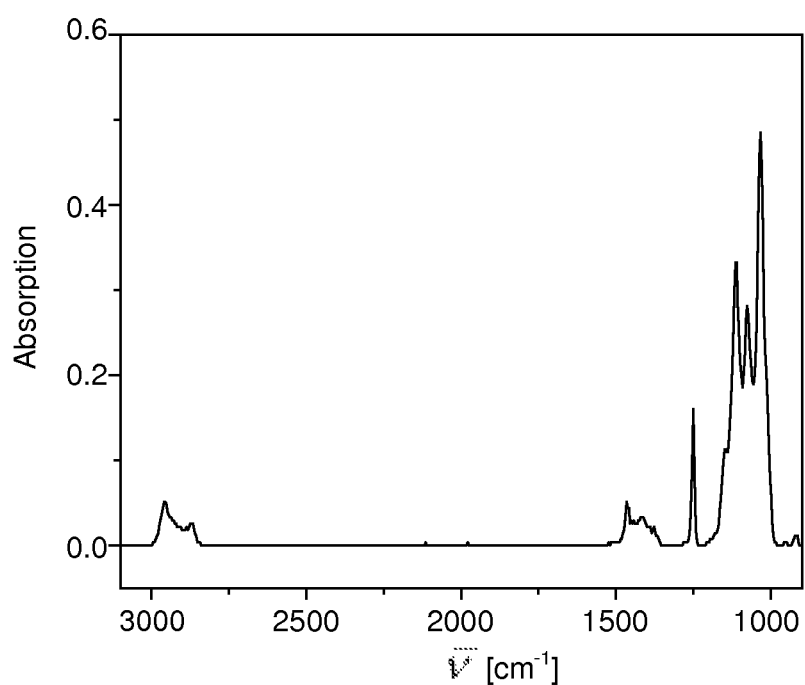
FIG. 2 shows an ATR-IR spectrum of a cross-linked polyadduct obtained according to the invention.

A mixture of tripropargylamine (Sigma-Aldrich) with 0.25 mol % copper(I) acetate was stirred for 2 h at room temperature. A stoichiometric quantity of 1,3-bis-(azidomethyl)ben- zene (prepared according to S. T. Abu-Orabi, R. E. Harmon, J. Chem. Eng. Data 31 (1986) 379-380) was then added. The reaction mixture was heated for 48 h to 32° C. to cure. The ATR-IR spectrum of the obtained cross-linked polyadduct is reproduced in FIG. 2 and shows complete conversion. The modulus of elasticity of this polyadduct was determined by means of nanoindentation. This is a high local resolution method for the mechanical characterization of solids which is based on the measurement of load and displacement during the elastic-plastic contact of a hard test piece (indenter) with the sample. The value of the modulus of elasticity of the cross-linked polyadduct determined by means of nanoindentation was 5.5 GPa. Comparison measurements using a dental resin, light-cured in a customary manner, based on a mixture of UDMA (90 wt.-%) and TEGDMA (10 wt.-%) resulted in a modulus of elasticity determined by means of nanoindentation of only 4.2 GPa.

Example 6

Filled Composite by Thermal Cross-Linking Cu(I)-Catalyzed Polycycloaddition of a Mixture of 1,3-bis-(azidomethyl)benzene and Tripropargylamine A mixture of tripropargylamine with copper(I) acetate (0.25 mol %) was stirred for 2 h at room temperature. A stoichiometric quantity of 1,3-bis-(azidomethyl)benzene was then added and pyrogenic silicic acid OX-50 (60 wt.-% relative to the total mixture, primary particle size 40 nm, Degussa) was incorporated into the obtained mixture. The reaction mixture was heated for 48 h to 32° C. to cure. The value of the modulus of elasticity of the obtained filled composite determined by means of nanoindentation was 11.7 GPa.

Example 7

Photo-Induced Cross-Linking Azide-Alkyne Polycycloadditions of a Mixture of 1,2-bis-(2-azidoethoxy)ethane and Tripropargylamine

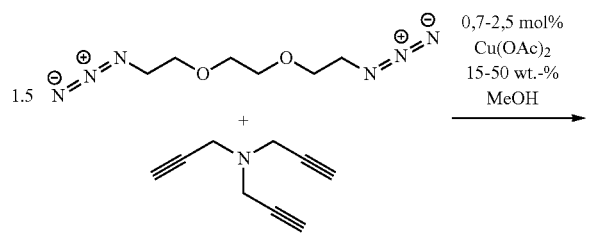

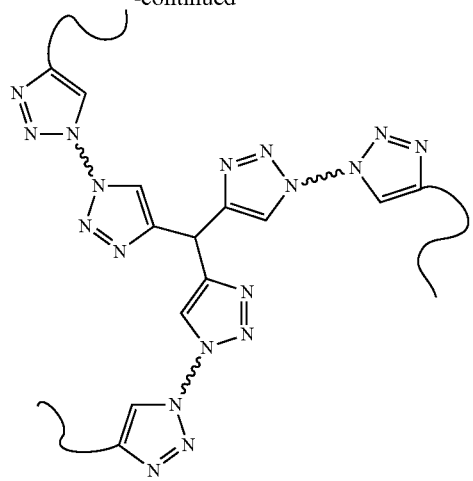
-continued

Copper(II) acetate (0.7-2.5 mol %) was dissolved in tripropargylamine within 5 min, as a result of which the color of the mixture changed from turquoise to colorless. Following addition of a stoichiometric quantity of 1,2-bis-(2-azidoethoxy) ethane and methanol (15 wt.-% relative to the total mixture), the reaction mixture was irradiated for 180 s in a light furnace (Dentacolor XS, Kulzer), which resulted in the formation of a colorless network polymer. The ATR-IR spectrum of the obtained cross-linked polymer is illustrated in FIG. 3 and shows complete conversion.

Example 8

Thermal Alkyne-Azide Cycloaddition and Photopolymerization of a Hybrid System Based on a Mixture of 1,3-bis-(azidomethyl)benzene, Tripropargylamine and N,N'-diethyl-1,3-bis-(acrylamido)propane System A

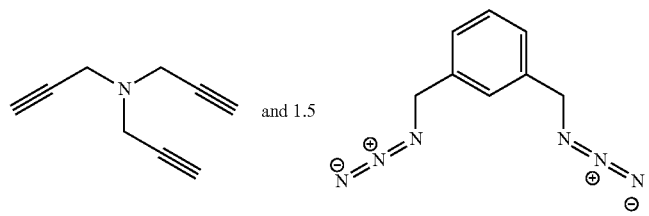

System B

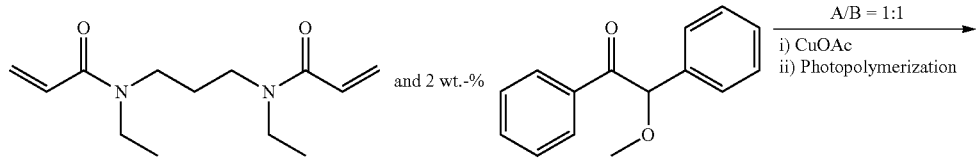

To prepare System A, a mixture of tripropargylamine (1 mol) and copper(I) acetate (0.16 mol %) was stirred for at least 2 h until a noticeable yellow coloring was recognizable, and then 1,3-bis-(azidomethyl)benzene (1.5 mol) was added. To prepare System B, the photoinitiator benzoyl methyl ether (2 wt.-%) was dissolved in N,N'-diethyl-1,3-bis-(acrylamido) propane within 30 min. Equal parts by weight of Systems A and B were then mixed (A/B=1:1). The obtained mixture was left to stand for 24 h at room temperature to cure, then irradiated in a light furnace (Dentacolor XS, Kulzer) for 540 s and finally heated for a further 24 h to 32° C. The ATR-IR spectrum of the obtained cross-linked polymer showed complete conversion. The value of the modulus of elasticity determined by means of nanoindentation was 5.1 GPa.

The invention claimed is:

1. Dental restorative material which comprises at least one compound of Formula I A-[X-Q-(Y-CG)$_n$]$_m$  Formula I, wherein A represents —O—, —N═, —NR$^3$—, ═N—N═, —NR$^3$—N═, ═N—NR$^3$—, —NR$^3$—NR$^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic C$_1$-C$_{50}$ radical which can be interrupted by one or more —O—, —S—, —NR$^3$—, —CO—O—, —O—CO—, —O—CO—O—, —CO—NR$^3$—, —NR$^3$—CO—, —O—CO—NR$^3$—, —NR$^3$—CO—O— or —NR$^3$—CO—NR$^3$—, cycloalkylene represents in each case independently a cycloaliphatic C$_3$-C$_{18}$ radical, heterocycloalkylene represents in each case independently a heterocycloaliphatic C$_3$-C$_{18}$ radical, arylene represents in each case independently an aromatic C$_6$-C$_{18}$ radical, heteroarylene represents in each case independently a heteroaromatic C$_3$-C$_{18}$ radical, cyclyl represents in each case independently cycloalkylene, heterocycloalkylene, arylene or heteroarylene and the indicated radicals in each case independently can carry one or more substituents, CG represents in each case independently an azide group N$_3$ or an alkyne group selected from the group consisting of —CR$^1$R$^2$—C≡CH,

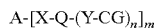

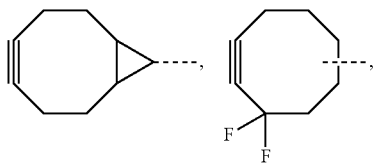

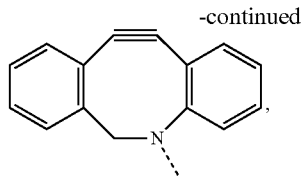

with the proviso that the dental restorative material comprises at least one compound of Formula I comprising an azide group and at least one compound of Formula I comprising an alkyne group as described above, Q in each case independently is missing or represents an (n+1)-valent linear or branched aliphatic C$_1$-C$_{20}$ alkylene radical which can be interrupted by one or more —O— or —S—, or a phenylene radical, wherein the indicated radicals in each case independently can carry one or more substituents, R$^1$, R$^2$ and R$^3$ in each case independently represent H or a C$_1$-C$_{10}$ alkyl radical, X and Y in each case independently are missing or represent —O—, —S—, —NR$^3$—, —CO—, —CO—O—, —O—CO—, —O—CO—O—, —CO—NR$^3$—, —NR$^3$—CO—, —O—CO—NR$^3$—, —NR$^3$—CO—O— or —NR$^3$—CO—NR$^3$—, m in each case independently can assume the values 2 to 6 and n in each case independently can assume the values 1 to 4, and wherein the dental restorative material further comprises a catalyst for the azide-alkyne cycloaddition and a light-inducible reducing agent and wherein the catalyst is a copper(II) compound.

2. Dental restorative material according to claim 1, wherein the copper(II) compound is selected from CuSO$_4$, CuCl$_2$, CuBr$_2$, Cu(OH)$_2$, Cu(OAc)$_2$, CuO, Cu(ClO$_4$)$_2$ and Cu(NO$_3$)$_2$ as well as the hydrates and THF adducts thereof.

3. Dental restorative material according to claim 1, which comprises as light-inducible reducing agent a photoinitiator selected from the group consisting of Norrish type I photoinitiators, titanocenes and α-diketones.

4. Dental restorative material which comprises at least one compound of Formula I A-[X-Q-(Y-CG)$_n$]$_m$  Formula I, wherein A represents —O—, —N═, —NR$^3$—, ═N—N═, —NR$^3$—N═, ═N—NR$^3$—, —NR$^3$—NR$^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic C$_1$-C$_{50}$ radical which can be interrupted by one or more —O—, —S—, —NR$^3$—, —CO—O—, —O—CO—, —O—CO—O—, —CO—NR$^3$—, —NR$^3$—CO—, —O—CO—NR$^3$—, —NR$^3$—CO—O— or —NR$^3$—CO—NR$^3$—, cycloalkylene represents in each case independently a cycloaliphatic C$_3$-C$_{18}$ radical, heterocycloalkylene represents in each case independently a heterocycloaliphatic C$_3$-C$_{18}$ radical, arylene represents in each case independently an aromatic C$_6$-C$_{18}$ radical, heteroarylene represents in each case independently a heteroaromatic C$_3$-C$_{18}$ radical, cyclyl represents in each case independently cycloalkylene, heterocycloalkylene, arylene or heteroarylene and the indicated radicals in each case independently can carry one or more substituents, CG represents in each case independently an azide group $N_3$ or an alkyne group selected from the group consisting of —$CR^1R^2$—C≡CH,

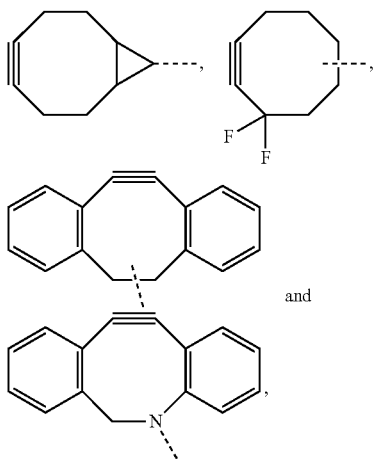

and with the proviso that the dental restorative material comprises at least one compound of Formula I comprising an azide group and at least one compound of Formula I comprising an alkyne group as described above, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and wherein the dental restorative material further which comprises one or more radically polymerizable monomers.

5. Dental restorative material according to claim 4, which comprises methyl-, ethyl-, hydroxyethyl-, butyl-, benzyl-, tetrahydrofurfuryl- or isobornyl(meth)acrylate, p-cumyl-phenoxyethylene glycol methacrylate (CMP-1E), bisphenol-A-di(meth)acrylate, Bis-GMA, ethoxylated or propoxylated bisphenol-A-dimethacrylate, UDMA, di-, tri- or tetraethylene glycol di(meth)acrylate, trimethylolpropane tri(meth)acrylate, pentaerythritol tetra(meth)acrylate, glycerol di- or tri(meth)acrylate, 1,4-butanediol di(meth)acrylate, 1,10-decanediol di(meth)acrylate ($D_3MA$), 1,12-dodecanediol di(meth)acrylate, and/or one or more N-mono- or -disubstituted acrylamides, N-ethylacrylamide, N,N-dimethylacrylamide, N-(2-hydroxyethyl)acrylamide, N-methyl-N-(2-hydroxyethyl)acrylamide, one or more N-monosubstituted methacrylamides, N-ethylmethacrylamide, N-(2-hydroxyethyl)methacrylamide, N-vinylpyrrolidone, one or more cross-linking allyl ethers, and/or one or more cross-linking pyrrolidones, 1,6-bis(3-vinyl-2-pyrrolidonyl)-hexane, one or more cross-linking bisacrylamides, methylene or ethylene bisacrylamide, one or more cross-linking bis(meth)acrylamides, N,N'-diethyl-1,3-bis(acrylamido)-propane, 1,3-bis(methacrylamido)-propane, 1,4-bis(acrylamido)-butane, 1,4-bis(acryloyl)-piperazine, or a mixture thereof.

6. Dental restorative material which comprises at least one compound of Formula I $$A\text{-}[X\text{-}Q\text{-}(Y\text{-}CG)_n]_m \qquad \text{Formula I,}$$

wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG represents in each case independently an azide group $N_3$ or an alkyne group selected from the group consisting of —$CR^1R^2$—C≡CH,

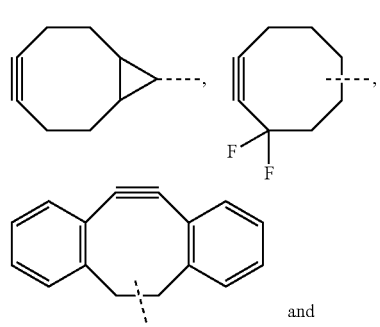

and

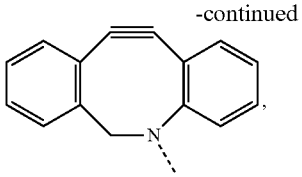

with the proviso that the dental restorative material comprises at least one compound of Formula I comprising an azide group and at least one compound of Formula I comprising an alkyne group as described above, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4 and wherein the dental restorative material further comprises organic and/or inorganic filler.

7. Dental restorative material which comprises at least one azide of Formula IA $$A-[X-Q-(Y-CG)_n]_m \qquad \text{Formula IA}$$

wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG in each case independently represents an azide group $N_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and at least one alkyne of Formula IB $$A-[X-Q-(Y-CG)_n]_m \qquad \text{Formula IB}$$

wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG represents in each case independently an alkyne group selected from the group consisting of —$CR^1R^2$—C≡CH,

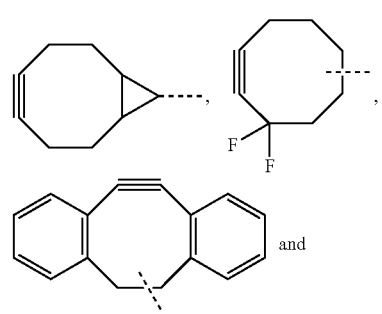

and

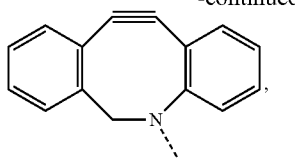

Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, in the following composition:

a) 0.1 to 80 wt.-% of a mixture of at least one azide of Formula IA and at least one alkyne of Formula IB,
b) 0.01 to 10 wt.-% catalyst,
c) 0 to 80 wt.-% co-monomer,
d) 0 to 90 wt.-% filler and
e) 0 to 70 wt.-% solvent.

8. A process for preparing a dental composite or dental restoration material, which process comprises providing a dental restorative material comprising reacting at least one azide of Formula IA and at least one alkyne of Formula IB as defined as follows:

$$A\text{-}[X\text{-}Q\text{-}(Y\text{-}CG)_n]_m \qquad \text{Formula IA}$$

wherein

A represents —O—, —N═, —$NR^3$—, ═N—N═, —$NR^3$—N═, ═N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein
  alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—,
  cycloalkylene represents in each case independently a cycloaliphatic $C_3$-$C_{18}$ radical,
  heterocycloalkylene represents in each case independently a heterocycloaliphatic $C_3$-$C_{18}$ radical,
  arylene represents in each case independently an aromatic $C_6$-$C_{18}$ radical,
  heteroarylene represents in each case independently a heteroaromatic $C_3$-$C_{18}$ radical,
  cyclyl represents in each case independently cycloalkylene, heterocycloalkylene, arylene or heteroarylene and
  the indicated radicals in each case independently can carry one or more substituents, CG in each case independently represents an azide group $N_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and at least one alkyne of Formula IB $$A\text{-}[X\text{-}Q\text{-}(Y\text{-}CG)_n]_m \qquad \text{Formula IB}$$

wherein

A represents —O—, —N═, —$NR^3$—, ═N—N═, —$NR^3$—N═, ═N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein
  alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—,
  cycloalkylene represents in each case independently a cycloaliphatic $C_3$-$C_{18}$ radical,
  heterocycloalkylene represents in each case independently a heterocycloaliphatic $C_3$-$C_{18}$ radical,
  arylene represents in each case independently an aromatic $C_6$-$C_{18}$ radical,
  heteroarylene represents in each case independently a heteroaromatic $C_3$-$C_{18}$ radical,
  cyclyl represents in each case independently cycloalkylene, heterocycloalkylene, arylene or heteroarylene and
  the indicated radicals in each case independently can carry one or more substituents, CG represents in each case independently an alkyne group selected from the group consisting of —$CR^1R^2$—C≡CH,

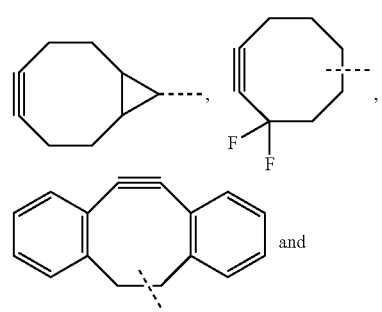

and

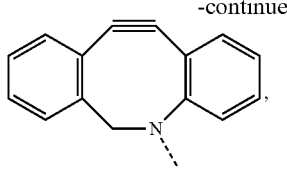

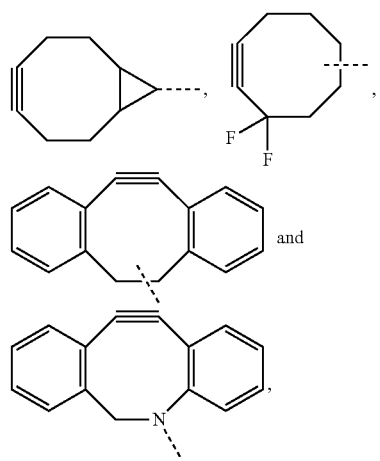

with the proviso that the dental restorative material comprises at least one compound of Formula I comprising an azide group and at least one compound of Formula I comprising an alkyne group as described above, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and and curing said dental restorative material.

9. A process for preparing a dental composite or dental restoration material, which process comprises providing a dental restorative material comprising at least one compound of Formula I

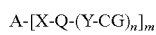    Formula I, wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG represents in each case independently an azide group $N_3$ or an alkyne group selected from the group consisting of —$CR^1R^2$—C≡CH, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and wherein said dental restoration material is an inlay, an onlay, a crown, a bridge or a veneering material.

10. A process for preparing a dental composite or dental restoration material, which process comprises reacting at least one azide of Formula IA and at least one alkyne of Formula IB as defined as follows:

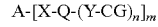    Formula IA wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG in each case independently represents an azide group $N_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and at least one alkyne of Formula IB A-[X-Q-(Y-CG)$_n$]$_m$    Formula IB wherein A represents —O—, —N═, —$NR^3$—, ═N—N═, —$NR^3$—N═, ═N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG represents in each case independently an alkyne group selected from the group consisting of —$CR^1R^2$—C≡CH,

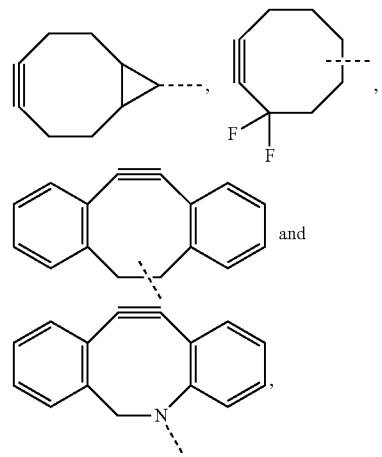

Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and wherein said dental composite or dental restoration material is an inlay, an onlay, a crown, a bridge or a veneering material.

11. Dental restorative material which comprises at least one azide of Formula IA A-[X-Q-(Y-CG)$_n$]$_m$    Formula IA wherein A represents —O—, —N═, —$NR^3$—, ═N—N═, —$NR^3$—N═, ═N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG in each case independently represents an azide group $N_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —NR$^3$—, —CO—, —CO—O—, —O—CO—, —O—CO—O—, —CO—NR$^3$—, —NR$^3$—CO—, —O—CO—NR$^3$—, —NR$^3$—CO—O— or —NR$^3$—CO—NR$^3$—, m in each case independently can assume the values 2 to 6 and n in each case independently can assume the values 1 to 4, and at least one alkyne of Formula IB A-[X-Q-(Y-CG)$_n$]$_m$      Formula IB wherein A represents —O—, —N=, —NR$^3$—, =N—N=, —NR$^3$—N=, =N—NR$^3$—, —NR$^3$—NR$^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —NR$^3$—, —CO—O—, —O—CO—, —O—CO—O—, —CO—NR$^3$—, —NR$^3$—CO—, —O—CO—NR$^3$—, —NR$^3$—CO—O— or —NR$^3$—CO—NR$^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG represents in each case independently an alkyne group selected from the group consisting of —CR$^1$R$^2$—C≡CH,

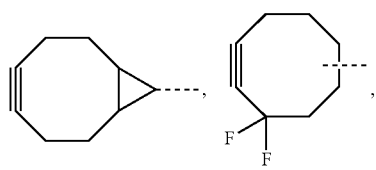

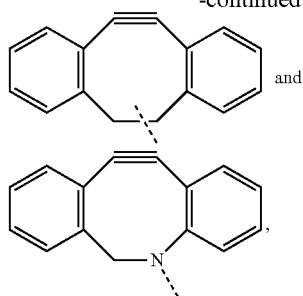

Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —NR$^3$—, —CO—, —CO—O—, —O—CO—, —O—CO—O—, —CO—NR$^3$—, —NR$^3$—CO—, —O—CO—NR$^3$—, —NR$^3$—CO—O— or —NR$^3$—CO—NR$^3$—, m in each case independently can assume the values 2 to 6 and n in each case independently can assume the values 1 to 4, in the following composition:

a) 1 to 60 wt.-% of a mixture of at least one azide of Formula IA and at least one alkyne of Formula IB,
b) 0.1 to 3 wt.-% catalyst,
c) 1 to 60 wt.-% co-monomer,
d) 10 to 80 wt.-% filler and
e) 1 to 50 wt.-% solvent.

12. Dental restorative material which comprises at least one azide of Formula IA A-[X-Q-(Y-CG)$_n$]$_m$      Formula IA wherein A represents —O—, —N=, —NR$^3$—, =N—N=, —NR$^3$—N=, =N—NR$^3$—, —NR$^3$—NR$^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —NR$^3$—, —CO—O—, —O—CO—, —O—CO—O—, —CO—NR$^3$—, —NR$^3$—CO—, —O—CO—NR$^3$—, —NR$^3$—CO—O— or —NR$^3$—CO—NR$^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG in each case independently represents an azide group $N_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and at least one alkyne of Formula IB A-[X-Q-(Y-CG)$_n$]$_m$   Formula IB wherein A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG represents in each case independently an alkyne group selected from the group consisting of —$CR^1R^2$—C≡CH,

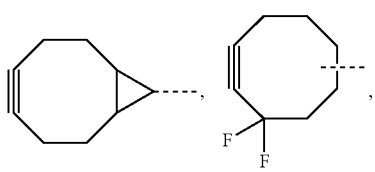

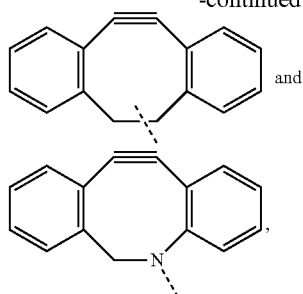

and

Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, in the following composition:

a) 5 to 50 wt.-% of a mixture of at least one azide of Formula IA and at least one alkyne of Formula IB, b) 0.2 to 2 wt.-% catalyst, c) 5 to 50 wt.-% co-monomer, d) 20 to 70 wt.-% filler and e) 5 to 20 wt.-% solvent.

13. Dental restorative material which comprises at least one azide of Formula IA A-[X-Q-(Y-CG)$_n$]$_m$   Formula IA wherein A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG in each case independently represents an azide group $N_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, and at least one alkyne of Formula IB $$A\text{-}[X\text{-}Q\text{-}(Y\text{-}CG)_n]_m \qquad \text{Formula IB}$$

wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, CG represents in each case independently an alkyne group selected from the group consisting of —$CR^1R^2$—C≡CH,

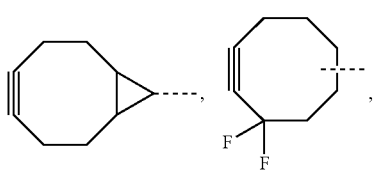

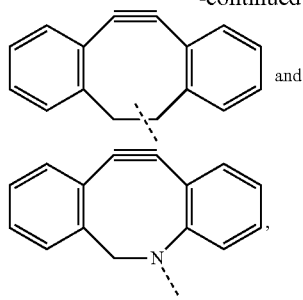

Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, $R^1$, $R^2$ and $R^3$ in each case independently represent H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4, in the following composition:
a) 10 to 40 wt.-% of a mixture of at least one azide of Formula IA and at least one alkyne of Formula IB,
b) 0.2 to 2 wt.-% catalyst,
c) 5 to 50 wt.-% co-monomer,
d) 20 to 70 wt.-% filler and
e) 5 to 20 wt.-% solvent.

14. Dental restorative material according to claim 1 wherein the one or more substituents comprise at least one of $C_1$-$C_5$ alkyl, OH, $OCH_3$ or $OCOCH_3$.

15. Dental restorative material according to claim 4 wherein the one or more substituents comprise at least one of $C_1$-$C_5$ alkyl, OH, $OCH_3$ or $OCOCH_3$.

16. Dental restorative material according to claim 6 wherein the one or more substituents comprise at least one of $C_1$-$C_5$ alkyl, OH, $OCH_3$ or $OCOCH_3$.

17. Dental restorative material according to claim 7 wherein the one or more substituents comprise at least one of $C_1$-$C_5$ alkyl, OH, $OCH_3$ or $OCOCH_3$.

18. Process according to claim 8 wherein the one or more substituents comprise at least one of $C_1$-$C_5$ alkyl, OH, $OCH_3$ or $OCOCH_3$.

19. Process according to claim 9 wherein the one or more substituents comprise at least one of $C_1$-$C_5$ alkyl, OH, $OCH_3$ or $OCOCH_3$.

20. Process according to claim 10 wherein the one or more substituents comprise at least one of $C_1$-$C_5$ alkyl, OH, $OCH_3$ or $OCOCH_3$.

21. Dental restorative material according to claim 11 wherein the one or more substituents comprise at least one of $C_1$-$C_5$ alkyl, OH, $OCH_3$ or $OCOCH_3$.

22. Dental restorative material according to claim 12 wherein the one or more substituents comprise at least one of $C_1$-$C_5$ alkyl, OH, $OCH_3$ or $OCOCH_3$.

23. Dental restorative material according to claim 13 wherein the one or more substituents comprise at least one of $C_1$-$C_5$ alkyl, OH, $OCH_3$ or $OCOCH_3$.

* * * * *